United States Patent [19]

Hasegawa et al.

[11] Patent Number: 4,983,385

[45] Date of Patent: Jan. 8, 1991

[54] OINTMENT BASE

[75] Inventors: Kenji Hasegawa; Nakashima Nakashima; Toru Eguchi; Ota Masako, all of Osaka, Japan

[73] Assignees: Sunstar Kabushiki Kaisha, Osaka; Lederle (Japan), Ltd., Tokyo, both of Japan

[21] Appl. No.: 250,543

[22] Filed: Sep. 29, 1988

[51] Int. Cl.[5] .............................................. A61K 7/48

[52] U.S. Cl. ...................................... 424/78; 424/80; 424/81; 514/944; 514/969

[58] Field of Search ............................ 424/78, 81, 80; 514/969, 944

[56] References Cited

U.S. PATENT DOCUMENTS 3,551,556 12/1970 Kliment ................................ 424/81
4,226,848 10/1980 Nagai et al. ........................... 424/78

FOREIGN PATENT DOCUMENTS 1136045 11/1982 Canada .................................. 424/81
0184389 11/1986 European Pat. Off. .
1075745 12/1974 Japan ..................................... 424/81
4119024 3/1978 Japan ..................................... 424/81
2126414 8/1982 Japan ..................................... 424/78
263314 11/1985 Japan .

*Primary Examiner*—Thurman K. Page
*Attorney, Agent, or Firm*—Wegner, Cantor, Mueller & Player

[57] ABSTRACT

An ointment base which comprises:

(a) a hydrogel formed by a water-soluble polymer and a material selected from the group consisting of water, a polyhydric alcohol and a mixture thereof;

(b) a methacrylate copolymer selected from a group consisting of dimethylaminoethyl methacrylate/-methyl methacrylate copolymer, ethyl methacrylate/chlorotrimethylammonium ethyl methacrylate copolymer or a mixture thereof; and (c) a solubilizer which dissolves the methacrylate copolymer but is incompatible with water and the polyhydric alcohol, a weight ratio of the methacrylate copolymer to the solubilizer being 1:2–1:25.

7 Claims, No Drawings

OINTMENT BASE

FILED OF THE INVENTION

The present invention relates to an ointment base. More particularly, it relates to a base for a pharmaceutical preparation or a cosmetic in the form of a paste or an ointment which is suitable for application on wet body surfaces such as a mucous membrane.

BACKGROUND OF THE INVENTION

Hitherto, various bases for pharmaceutical preparations or cosmetics have been known. However, when they are applied as pharmaceutical preparations or cosmetics on wet body surfaces such as a mucous membrane, they have insufficient adhesion to the applied site and insufficient local retentivity.

For example, as ointment bases for pharmaceutical preparations or cosmetics to be applied on wet body surfaces, those obtained by incorporating fatty base materials such as liquid paraffin, vaseline and the like with water-absorbent polymers such as gelatin, sodium carboxymethyl-cellulose and the like have been used. However, they have several problems such as inferior adhesion to an applied site, large particle size of solids content and pain upon application. As a means for solving these problems, an ointment base to which polyacrylic acid or a salt thereof is added has been proposed (see Japanese Patent Kokai Nos. 52-117416 and 53-86011). However, such an ointment base still has some problems. For example, it has inferior halotolerant properties, and a pharmacologically active agent or an active ingredient formulated tends to be unstable due to interaction with polyacrylic acid.

OBJECTS OF THE INVENTION

Under these circumstances, the present inventors have studied intensively to obtain an ointment base which has sufficient adhesion to an applied site and local retentivity even when it is applied on a wet body surface, and provides prolonged action of a pharmacologically active agent or an active ingredient without above defects and problems. As a result, the present inventors have found that a desired ointment base can be obtain by combining a hydrogel with a certain methacrylate copolymer and a solubilizer.

That is, the main object of the present invention is to provide an ointment base which is suitable for application on wet body surfaces such as a mucous membrane.

This object as well as other objects and advantages of the present invention will become apparent to those skilled in the art from the following description.

SUMMARY OF THE INVENTION

The present invention provides an ointment base which comprises:

(a) a hydrogel formed by a water-soluble polymer and a material selected from the group consisting of water, a polyhydric alcohol and a mixture thereof;

(b) a methacrylate copolymer selected from a group consisting of dimethylaminoethyl methacrylate/methyl methacrylate copolymer, ethyl methacrylate/chlorotrimethylammonium ethyl methacrylate copolymer or a mixture thereof: and (c) a solubilizer which dissolves the methacrylate copolymer but is incompatible with water and the polyhydric alcohol, a weight ratio of the methacrylate copolymer to the solubilizer being 1 : 2 to 1 : 25.

The ointment base of the present invention shows sufficient adhesion and local retentivity when it is applied as a pharmaceutical preparation or a cosmetic on a wet body surface without such problems of, for example, pain upon application, inferior halotolerant properties, less stability of a pharmacologically active agent or an active ingredient formulated.

The present inventors' co-pending U.S. Pat. Application Ser. No. 801,812 filed Nov. 26, 1985 discloses a pharmaceutical composition containing minocycline in a stable state which is prepared by using a base fallen within the scope of the present invention. The U.S. Pat. Application is corresponding to European Pat. Application EP 0184389 (A2) published June 11, 1986.

DETAILED DESCRIPTION OF THE INVENTION

The water-soluble polymer which forms the component (a), hydrogel, of the ointment base of the present invention includes natural polymers such as gum arabic, guar gum, tragacanth gum, locust bean gum, carrageenan, agar, starch, c-starch, dextrin, alginic acid, alginate, pectin, xanthan gum, succinoglucan, dextran, pullulan, gelatin, chitin, chitosan, etc.; semi-synthetic polymers such as carboxymethyl cellulose, hydroxyethyl cellulose, hydroxypropyl cellulose, hydroxypropylmethyl cellulose, methyl cellulose, salts thereof, propylene glycol alginate, carboxymethylstarch, etc. synthetic polymers such as polyvinyl pyrrolidone, polyvinyl alcohol, carboxyvinyl polymer, polyacrylic acid and salts thereof, polyvinyl methyl ether, methoxyethylene/maleic anhydride copolymer, starch/acrylic acid graft copolymer, etc: a mixture thereof and the like. The water-soluble polymer may be used in the amount sufficient to provide a paste or an ointment having appropriate viscosity. Generally, it is used in the amount of 0.1 to 10% by weight based on the total weight of the resulting ointment base.

The polybydric alcohol which forms the component (a), hydrogel, includes, for example, glycerin, ethylene glycol, diethylene glycol, propylene glycol, dipropylene glycol, hexylene glycol, 1,5-pentanediol, 1,3-butylene glycol and the like. The polyhydric alcohol can be optionally mixed with water. Water and/or the polyhydric alcohol can be used in such an amount that they form a hydrogel having desired properties by dissolving the water-soluble polymer and generally in the amount suitable for formation of a gel having a water-soluble polymer content of 0.1 to 25% by weight.

The components (b), dimethylaminoethyl methacrylate/ethyl methacrylate copolymer and ethyl methacrylate/chlorotrimethylammonium ethyl methacrylate copolymer, are copolymers known as trade names of Eudragit E and RS, respectively. It can be used alone or in combination thereof. The methacrylate copolymer has been used heretofore as a resin having film forming ability for a coating formulation. In the present invention, it contributes to improve adhesion onto a wet body surface and local retentivity of the ointment base, and can be used in an amount of 0.5 to 20% by weight based on the total weight of the ointment base in view of its properties.

Various kinds of solubilizers for the methacrylate copolymer have been known. In the present invention, from the viewpoint of properties of the resulting ointment base, the solubilizer should dissolve the copolymer but is incompatible with the hydrogel, i.e. water and the polyhydric alcohol. Examples of the solubilizer include lower alcohol esters such as triacetin, tributyrin, diacetyl ethylene glycol, di-isopropyl adipate, diethyl sebacate, diethyl phthalate, dibutyl phthalate dibutyl succinate: clove oil and the like. They can also be used alone or in combination thereof. Generally, they are used in an amount of 5 to 50% by weight, preferably, 10 to 20% by weight based on the total weight of the ointment base. The weight ratio of the methacrylate copolymer : the solubilizer should be 1 : 2 to 1 : 25 in view of improvement of adhesion and retentivity.

The ointment base of the present invention can be prepared according to a conventional technique. For example, the base can be prepared by mixing the water-soluble polymer and water and/or the polyhydric alcohol and, if necessary heating to form the hydrogel, mixing the resulting hydrogel with the methacrylate copolymer which had been separately dissolved in the solubilizer, and homogeneously blending the mixture. Alternatively, the hydrogel formed may be admixed with the solubilizer and the finely ground methacrylate copolymer in optional order.

The ointment base of the present invention can be used for production of a pharmaceutical preparation or a cosmetic in the form of an ointment or a paste which is suitable to be applied on a wet body surface, for example, in the oral cavity, lips, eyes, vagina, etc. according to a conventional technique. For example, the ointment base of the present invention can be incorporated with a pharmacologically active agent or an active ingredient, for example, antalgesics such as ethyl aminobenzoate, ethyl p-piperidylacetylaminobenzoate, dibucaine hydrochloride, lidocaine hydrochloride, tetracaine hydrochloride, diethylaminoethyl p-butylaminobenzoate, clove oil, eugenol, etc.: antibacterial or antifungal agents such as aminoglycoside antibiotics, clindamycin, chloramphenicol. macrolides, tetracycline, doxycycline, iodide compounds, chlorophenol compounds, acrinol, dequalinium, benzalkonium, benzethonium, cetyl pyridinium, chlorhexidine, sulfa drugs, metronidazole, ofloxacin, sanguinarine, etc.: nonsteroidal antiinflammatory drugs such as indomethacin, sulindac, tolmetin, acemetacin, ibuprofen, flurbiprofen, ketoprofen, naproxen, fenoprofen, pranoprofen, tiaprofenic acid, fenbufen, benoxaprofen, indoprofen, aspirin, aspirin aluminum, diflunisal, diclofenac sodium, alclofenac, fentiazac, amfenac sodium, mepirizole, tiaramide, tinoridine, benzydamine, perisoxal bone and mineral metabolic drugs such as 1-hydroxyethane-1,1-diphosphonate, dichloromethanediphosphonate, 3-amino-1-hydroxypropane-1,1-diphosphonate, 1,25-dihydroxycholecalciferol, 24,25-dihydroxycholecalciferol, 1,24-dihydroxycholecalciferol, prometadin hydrochloride, sodium aurothiomalate, prostagrandin $E_1$, prostagrandin $E_2$, prostagrandin $F_{2\alpha}$, calcitonin, parathyroid hormone, steroidal hormone, insulin, sex hormones, growth hormones, epidermal growth factor, nerve growth factor, cartilage derived factor, bone morphogenetic protein, osteocalcin, osteonectin, fibronectin, laminin, collagen, interleukin 1, interleukin 2, interleukin 3, osteoclast activating factor; optionally, together with other additives such as stabilizers, flavors and the like to obtain a pharmaceutical preparation or a cosmetic.

The following Experiment, Examples and Reference Examples further illustrate the present invention in detail but are not construed to be limit the scope thereof.

EXPERIMENT

Various ointment bases were prepared by formulating different amounts of triacetin and Eudragit RS with a hydrogel formed by hydroxyethyl cellulose (2% by weight based on the total weight) and glycerin.

Adhesion and retentivity on the mucous membrane in the oral cavity of these ointment bases were evaluated according to the partially modified dissolution test described in Japanese Pharmacopoeia. That is, a metallic plate (50×50 mm) was welded to the lower part of the revolving shaft of the testing device used in the dissolution test of the Pharmacopoeia, and the mucous membrane of bursa buccalis removed from a hamster was spread and fixed on the plate. On the surface of the mucosa, each ointment base (1 g) was applied and the shaft was rotated at 100 rpm in human saliva at 37° C. Then, adhesion and retentivity were evaluated by the naked eye. The results are shown in Table 1.

TABLE 1

| Triacetin | Eudragit RS (wt%) | | | | | |
|---|---|---|---|---|---|---|
| (wt%) | 0.1 | 0.5 | 2.0 | 5.0 | 10.0 | 20.0 |
| 2.5 | D | D | D | D | D | D |
| 5.0 | D | G | G | D | D | D |
| 10.0 | D | G | G | G | D | D |
| 25.0 | D | D | G | G | G | D |
| 50.0 | D | D | G | G | G | G |
| 75.0 | D | D | D | P | P | P |

D: dispersed
G: good
P: peeled off

As shown in Table 1, when the amount of triacetin and Eudragit RS are 5 to 50% by weight and 0.5 to 20% by weight, respectively, and the weight ratio of triacetin : Eudragit RS is in the range from 1 : 2 to 1 : 25, good retentivity can be obtained. When the amount of triacetin becomes more than 50% by weight, adhesion is remarkably impaired.

EXAMPLE 1

Glycerin (1 kg) was heated to 120° C. Carrageenan (10 g) was added to glycerin and dissolved therein to obtain a hydrogel. A solution of Eudragit E (40 g) in diethyl sebacate (100 g) was admixed with the hydrogel to obtain a desired ointment base.

EXAMPLE 2

Xanthan gum (5 g) was dissolved in distilled water (1 kg) to obtain a hydrogel. A solution of Eudragit E (20 g) in diethyl phthalate (80 g) was admixed with the hydrogel to obtain a desired ointment base.

EXAMPLE 3

Hydroxypropyl cellulose (80 g) was dissolved in distilled water (1 kg) to obtain a hydrogel. The hydrogel was admixed with triacetin (200 g) with stirring, followed by Eudragit RS powder (30 g, finely ground to smaller than 48 mesh) to obtain a desired ointment base.

EXAMPLE 4

Glycerin (1 kg) was heated to 150° C. Hydroxyethyl cellulose (40 g) was dissolved therein to obtain a hydrogel. The resulting hydrogel was cooled to 60° C. and admixed with a solution of Eudragit RS (25 g) in triacetin (150 g) to obtain a desired ointment base.

EXAMPLE 5

Sodium carboxymethyl cellulose (50 g) was dispersed in propylene glycol (100 g) and distilled water (900 g) was added thereto. Dissolution was effected to obtain a hydrogel. A solution of Eudragit RS (100 g) in triacetin (400 g) was admixed with the resulting hydrogel to obtain a desired ointment base.

EXAMPLE 6

Polyvinyl pyrrolidone (100 g) was dissolved in ethylene glycol (1 kg) to obtain a hydrogel. A solution of Eudragit RS (10 g) in triacetin (80 g) was added to the hydrogel to obtain a desired ointment base.

EXAMPLE 7

Carbopol 941 (20 g, manufactured by the B. F. Goodrich Co.) was dispersed in glycerin (50 g). Distilled water (900 g) was added thereto and the mixture was nutralized with an aqueous solution of triethanolamine to obtain a hydrogel. A solution of Eudragit RS (20 g) in triacetin (200, g) was admixed with the hydrogel to obtain a desired ointment base.

REFERENCE EXAMPLE 1

Cetyl pyridinium chloride (5% by weight) was formulated in the ointment base of Example 4 to obtain an antibacterial composition. According to the above method, adhesion and retentivity of this composition was evaluated. The same evaluation was carried out by using a control composition prepared by formulating 5% by weight of cetyl pyridinium chloride into the hydrophilic ointment of Japanese Pharmacopoeia. As the result, the former antibacterial composition continued to adhere to the membrane for 109 minutes, whereas the latter control composition removed from the membrane 38 minutes after start of rotation.

Further, the former antibacterial composition continued to release the active ingredient even 40 hours after application, whereas the latter control composition released 100 % of the active ingredient within 1 hours.

What is claimed is:

1. An ointment base for a wet body surface which comprises:

(a) a hydrogel formed by (i) a water-soluble polymer and a material selected from the group consisting of water, a polyhydric alcohol and (ii) a mixture thereof;

(b) a methacrylate copolymer selected from a group consisting of dimethylaminoethyl methacrylate/-methyl methacrylate copolymer, ethyl methacrylate/chlorotrimethylammonium ethyl methacrylate copolymer or a mixture thereof; and (c) a solubilizer which dissolves the methacrylate copolymer but is incompatible with water and the polyhydric alcohol, a weight ratio of the methacrylate copolymer to the solubilizer being 1:2 to 1:25.

2. An ointment base according to claim 1, wherein the water-soluble polymer is a member selected from the group consisting of gum arabic, guar gum, tragacanth gum, locust bean gum, carrageenan, agar, starch, α-starch, dextrin, alginic acid, alginate, pectin, xanthan gum, succinoglucan, dextran, pullulan, gelatin, chitin, chitosan, carboxymethyl cellulose, hydroxyethyl cellulose, hydroxypropyl cellulose, hydroxypropylmethyl cellulose, methyl cellulose, salts thereof, propylene glycol alginate, carboxymethylstarch, polyvinyl pyrrolidone, polyvinyl alcohol, carboxyvinyl polymer, polyacrylic acid and salts thereof, polyvinyl methyl ether, methoxyethylene maleic anhydride copolymer, starch/acrylic acid graft copolymer, and a mixture thereof.

3. An ointment base according to claim 1, wherein the polyhydric alcohol is alkane-diol or alkane-triol having 2 to 6 carbon atoms.

4. An ointment base according to claim 1, wherein the polyhydric alcohol is a member selected from the group consisting of glycerin, ethylene glycol, diethylene glycol, propylene glycol, dipropylene glycol, hexylene glycol, 1,5-pentenediol, 1,3-butylene glycol, and a mixture thereof.

5. An ointment base according to claim 1, wherein the solubilizer is member selected from the group consisting of esters of lower polyhydric alcohol having 2 to 4 carbon atoms, esters of lower fatty acid having 2 to 4 carbon atoms, esters of lower alcohol having 2 to 4 carbon atoms and esters of dicarboxylic acid having 4 to 10 carbon atoms.

6. An ointment base according to claim 1, wherein the solubilizer is member selected from the group consisting of triacetin, tributyrin, diacetyl ethylene glycol, di-isopropyl adipate, diethyl sebacate, diethyl phthalate, dibutyl phthalate dibutyl succinate, clove oil, and a mixture thereof.

7. An ointment base according to claim 1 wherein the base contains 0.1 to 10% by weight of the water-soluble polymer, 0.5 to 20% by weight of the methacrylate copolymer and 5 to 50% by weight of the solubilizer.

* * * * *

UNITED STATES PATENT AND TRADEMARK OFFICE

CERTIFICATE OF CORRECTION

PATENT NO. : 4,983,385

DATED : January 8, 1991

INVENTOR(S) : Kenji HASEGAWA et al.

It is certified that error appears in the above-identified patent and that said Letters Patent is hereby corrected as shown below:

In the left hand column of the title page between Item [22] (Filed: Sep. 29, 1988) and Item [51] (Int. Cl.) insert:

--Related U.S. Application Data

[63] Continuation of Ser. No. 051,291, May 19, 1987, Abandoned.--

In Column 1 between the title "OINTMENT BASE" and the heading "FIELD OF THE INVENTION" insert:

--This is a Continuation application of United States application Ser. No. 051,291, filed May 19, 1987.--

Signed and Sealed this

Twenty-fifth Day of August, 1992

*Attest:*

DOUGLAS B. COMER

*Attesting Officer* *Acting Commissioner of Patents and Trademarks*